United States Patent [19]
Ravikumar et al.

[11] Patent Number: 6,124,450
[45] Date of Patent: Sep. 26, 2000

[54] PROCESSES AND INTERMEDIATES FOR PHOSPHOROUS-CONTAINING COVALENT LINKAGES

[75] Inventors: Vasulinga Ravikumar, Carlsbad, Calif.; Dennis Mulvey, Conroe, Tex.; Douglas L. Cole, San Diego; Phillip Dan Cook, Carlsbad, both of Calif.

[73] Assignee: ISIS Pharmaceuticals, Inc., Carlsbad, Calif.

[21] Appl. No.: 09/123,138

[22] Filed: Jul. 27, 1998

Related U.S. Application Data

[62] Division of application No. 08/789,443, Jan. 27, 1997, Pat. No. 5,847,106, which is a division of application No. 08/099,075, Jul. 29, 1993, Pat. No. 5,614,621.

[51] Int. Cl.$^7$ ............................ C07H 21/00; C07H 21/02
[52] U.S. Cl. ..................... 536/25.34; 536/25.3; 556/436; 556/449
[58] Field of Search ............................... 536/25.34, 25.3; 556/436, 449

[56] References Cited

U.S. PATENT DOCUMENTS

| | | | |
|---|---|---|---|
| 4,458,066 | 7/1984 | Caruthers et al. | 536/25.34 |
| 4,725,677 | 2/1988 | Koster et al. | 536/27 |
| 4,845,205 | 7/1989 | Huynh Dinh et al. | 536/28 |
| 4,910,300 | 3/1990 | Urdea et al. | 536/28.5 |
| 5,113,005 | 5/1992 | Celebuski | 556/449 |
| 5,159,095 | 10/1992 | Celebuski | 556/436 |
| 5,614,621 | 3/1997 | Ravikumar et al. | 536/25.34 |

FOREIGN PATENT DOCUMENTS

| | | |
|---|---|---|
| WO 91/04983 | 4/1991 | WIPO . |
| WO 92/21689 | 12/1992 | WIPO . |

OTHER PUBLICATIONS

Alul et al., "Oxalyl–CPG: a labile support for synthesis of sensitive oligonucleotide derivatives", *Nucl. Acids. Res.*, 1991, 19, 1527–1532.

Beaucage et al., "Advances in the Synthesis of Oligonucleotides by the Phosphoramidite Approach", *Tetrahedron*, 1992, 48, 2223–2311.

Celebuski, et al., "Synthesis and Utility of a DNA Phosphorylating Agent Based on 2–(Triphenylsilyl)ethanol", *J. Org. Chem.*, 1992, 57, 5535–5538.

Honda, et al., "2–Diphenylmethylsilylethyl Group as a New Protecting Group of Internucleotidic Phosphates in Oligonucleotide Synthesis", *Tetrahedron Letters*, 1981, 2093–2096.

Iyer et al., "3H–1,2–Benzodithiole–3–one 1,1–Dioxide as an Improved Sulfurizing Reagent in the Solid–Phase Synthesis of Oligodeoxyribonucleoside Phosphorothioates", *J. Am. Chem. Soc.*, 1990, 112, 1253–1254.

Iyer et al., "The Automated Synthesis of Sulfur–Containing Oligodeoxyribonucleotides Using 3H–1,2–Benzodithiol–3–one 1,1–Dioxide as a Sulfur–Transfer Reagent", *J. Org. Chem.*, 1990, 55, 4693–4699.

Kamer et al., "An Efficient Approach Toward the Synthesis of Phosphorothioate Diesters Via the Schonberg Reaction", *Tetra. Lett.*, 1989, 30, 6757–6760.

March, "Advanced Organic Chemistry", John Wiley & Sons, New York, Third Edition, 1985, Chapter 1, pp. 16–18 and Chapter 9, pp. 237–239.

Rao et al., "Dibenzoyl Tetrasulphide—A Rapid Sulphur Transfer Agent in the Synthesis of Phosphorothioate Analogues of Oligonucleotides", *Tetra. Lett.*, 1992, 33, 4839–4842.

Streitwieser and Heathcock, "Introduction to Chemistry", Second Edition, 1981, Chapter 15, 437–440.

Takaku, et al., "Use of 1,1,1,3,3,3–Hexafluoro–2–Propyl Protecting Group in the Synthesis of DNA Fragments Via Phosphoramidite Intermediates", *Tetrahedron Letters*, 1988, 29, 81–84.

Vu et al., "Internucleotide Phosphite Sulfurization with Tetraethyl Thiuram Disulfide. Phosphorothioate Oligonucleotide Synthesis Via Phosphoramidite Chemistry", *Tetra. Lett.*, 1989, 32, 3005–3008.

Wright et al., "Large Scale Synthesis of Oligonucleotides via Phosphoramidite Nucleosides and a High–Loaded Polystyrene Support", *Tetra. Lett.*, 1993, 32, 3373–3376.

Sawabe et al., "Use of 2–Trimethylsilylethyl as a Protecting Group in Phosphate Monoester Synthesis", *Tetra. Lett.*, 1992, 33(50), 7685–7686.

Hartle, R.J., "Structural Stabilities of the Trimethylsilylmethyl and Neopentyl Groups in the Preparation of Phosphonyl Dichlorides", *J. Org. Chem.*, 1966, 31, 4288–4290.

Kawashima, T. et al., "Fluoride Ion–Induced Horner–Emmons Reaction of α–Silylalklphosphonic Derivatives with Carbonyl Compounds", *Bull. Chem. Soc. Japan*, 1987, 60, 1131–1137.

Sonnek, G. et al., "Aluminum alkyls with heteroatoms; preparation of phosphonic acid diamides. Part XI", *Chem. Abstracts*, 1981, 95, 95:204061, p. 694.

Ravikumar, V.T. et al., "Synthesis of Oligonucleotides Via Phosphoramidite Approach Utilizing 2–Diphenylmethylsilylethyl (DPSE) as a Phosphorus Protecting Group", *Tetrahedron*, 1994, 50(31), 9255–9266.

Ravikumar, V.T. et al., "2–Diphenylmethylsilyethyl (DPSE): a versatile protecting group for oligodeoxyribonucleotide synthesis", *Gene*, 1994, 149, 157–161.

Sawabe, A. et al., "Use of 2–Trimethylsilylethyl as a Protecting Group in Phosphate Monoester Synthesis", *Tetra. Lett.*, 1992, 33(50), 7685–7686.

Wada et al., "2–(Trimethylsilyl)ethyl as a Phosphate Protecting Group in Oligonucleotide Synthesis", *Tetra. Lett.*, 1994, 35(5), 757–760.

*Primary Examiner*—James O. Wilson
*Attorney, Agent, or Firm*—Woodcock Washburn Kurtz Mackiewicz & Norris LLP

[57] ABSTRACT

Synthetic processes are provided wherein substituted silylalkyl phosphoramidites serve as coupling reagents for preparing phosphate, phosphorothioate, and other phosphorous-containing covalent linkages. Also provided are synthetic intermediates useful in such processes.

9 Claims, No Drawings

PROCESSES AND INTERMEDIATES FOR PHOSPHOROUS-CONTAINING COVALENT LINKAGES

This patent application is a division of application Ser. No. 08/789,443, filed on Jan. 27, 1997 (now U.S. Pat. No. 5,847,106), which is a division of application Ser. No. 08/099,075, filed on Jul. 29, 1993 (now U.S. Pat. No. 5,614,621).

FIELD OF THE INVENTION

This invention is directed to novel processes for preparing phosphate, phosphorothioate, and other phosphorous-containing covalent linkages. The invention additionally is directed to novel synthetic intermediates useful in such processes.

BACKGROUND OF THE INVENTION

The chemical literature discloses numerous processes for coupling nucleosides through phosphorous-containing covalent linkages to produce oligonucleotides of defined sequence. One of the most popular processes is the phosphoramidite technique (see, e.g., Beaucage, et al., *Tetrahedron* 1992, 48, 2223 and references cited therein), wherein a nucleoside or oligonucleotide having a free hydroxyl group is reacted with a protected cyanoethyl phosphoramidite monomer in the presence of a weak acid to form a phosphite-linked structure. Oxidation of the phosphite linkage followed by hydrolysis of the cyanoethyl group yields the desired phosphate or phosphorothioate linkage.

The phosphoramidite technique, however, is not without its disadvantages. For example, cyanoethyl phosphoramidite monomer is quite expensive. Although considerable quantities of monomer go unreacted in a typical phosphoramidite coupling, unreacted monomer can be recovered, if at all, only with great difficulty. Also, acrylonitrile, the by-product of deprotection of the cyanoethoxy group on the phosphate group is carcinogenic and in some cases acts as a Michael acceptor to form undesired side-products.

Consequently, there remains a need in the art for synthetic methods that will overcome these problems.

OBJECTS OF THE INVENTION

It is an object of the present invention to provide processes for preparing phosphate, phosphorothioate, and other phosphorous-containing covalent linkages.

It is another object of this invention to provide processes that can be adapted for automated control.

It is a further object to provide starting materials and synthetic intermediates useful in such processes.

It is yet another object to provide starting materials and reaction products that can be recovered and recycled for further use.

It is still another object to provide processes that engender stereoselectivity in their reaction products.

SUMMARY OF THE INVENTION

These and other objects are satisfied by the present invention, which provides processes for preparing phosphorous-containing covalent linkages through use of substituted silylalkyl phosphoramidite coupling reagents. In preferred embodiments, non-racemic products are prepared by processes that comprise contacting a protected nucleoside having formula I with a coupling reagent having formula $[(R_N)_2N]_2PO(CH_2)_xSi(R_S)_3$ for a time and under reaction conditions effective to form a silylalkyl phosphoramidite monomer having formula II, wherein:

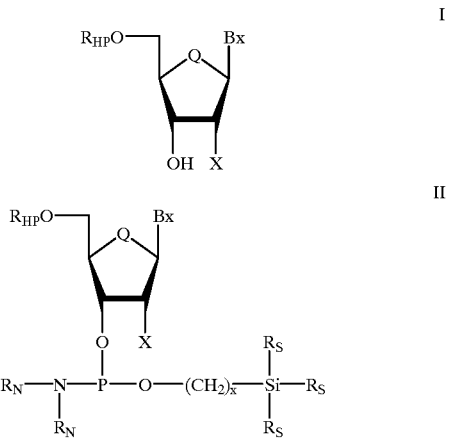

each Q is, independently, O, S, $CH_2$, CHF or $CF_2$;

each $B_x$ is, independently, a nucleosidic base;

each X is, independently, H, OH, alkyl, substituted alkyl, alkaryl or aralkyl, F, Cl, Br, CN, $CF_3$, $OCF_3$, OCN, O-alkyl, S-alkyl, N-alkyl, O-alkenyl, S-alkenyl, N-alkenyl, $SOCH_3$, $SO_2CH_3$, $ONO_2$, $NO_2$, $N_3$, $NH_2$, heterocycdoalkyl, heterocycloalkaryl, aminoalkylamino, polyalkylamino or substituted silyl, an RNA cleaving group, a group for improving the pharmacokinetic properties of an oligonucleotide, or a group for improving the pharmacodynamic properties of an oligonucleotide;

$R_{HP}$ is a hydroxyl protecting group;

each $R_N$ is, independently, alkyl having 1 to about 10 carbon atoms;

each $R_S$ is, independently, alkyl having 1 to about 10 carbon atoms or aryl having 6 to about 10 carbon atoms; and x is 1 to about 7.

Such monomers then are contacted with support-bound nucleosides having formula III ((P)=solid support) for a time and under reaction conditions effective to form support-bound, phosphite dimers having formula IV.

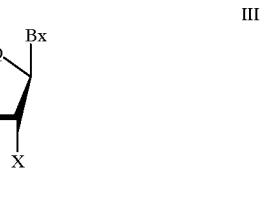

-continued

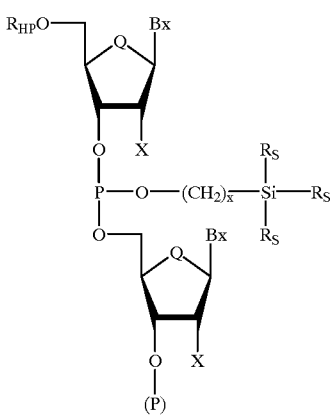

(IV)

Dimers having formula IV are contacted with an oxidizing agent for a time and under reaction conditions effective to form oxidation products having formula V (Z=O or S), which are contacted with aqueous base to form solution-phase silyl reaction products. These reaction products are treated with fluoride ion to produce phosphate and phorphorothioate dimers having formula VI.

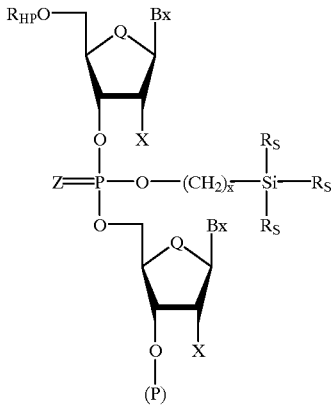

(V)

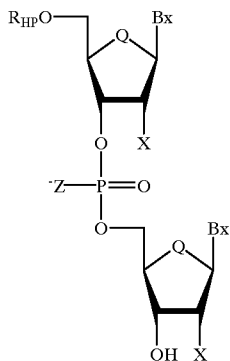

(VI)

DETAILED DESCRIPTION OF THE INVENTION

This invention provides new and improved processes for the preparation of phosphorous-containing covalent linkages and intermediates useful in such processes. Utilizing these processes and intermediates, phosphate and phosphorothioate oligonucleotides are prepared from a plurality of nucleoside or oligonucleotide subunits. The nucleoside subunits may be "natural" or "synthetic" moieties. Thus, in the context of this invention, the term "oligonucleotide" in a first instance refers to a polynucleotide formed from a plurality of linked nucleoside units. The nucleosides are formed from naturally occurring bases and pentofuranosyl sugar groups. The term "oligonucleotide" thus effectively includes naturally occurring species or synthetic species formed from naturally occurring subunits.

Oligonucleotides according to the invention also can include modified subunits. Representative modifications include modification of a heterocyclic base portion of a nucleoside or a sugar portion of a nucleoside. Exemplary modifications are disclosed in the following U.S. patent applications: Ser. No. 463,358, filed Jan. 11, 1990, entitled Compositions And Methods For Detecting And Modulating RNA Activity; Ser. No. 566,977, filed Aug. 13, 1990, entitled Sugar Modified Oligonucleotides That Detect And Modulate Gene Expression; Ser. No. 558,663, filed Jul. 27, 1990, entitled Novel Polyamine Conjugated Oligonucleotides; Ser. No. 558,806, filed Jul. 27, 1991, entitled Nuclease Resistant Pyrimidine Modified Oligonucleotides That Detect And Modulate Gene Expression and Ser. No. PCT/US91/00243, filed Jan. 11, 1991, entitled Compositions and Methods For Detecting And Modulating RNA Activity. Each of these patent applications are assigned to the assignee of this invention. The disclosure of each is incorporated herein by reference.

The term oligonucleotide thus refers to structures that include modified portions, be they modified sugar moieties or modified base moieties, that function similarly to natural bases and natural sugars. Representative modified bases include deaza or aza purines and pyrimidines used in place of natural purine and pyrimidine bases; pyrimidines having substituent groups at the 5 or 6 position; purines having altered or replacement substituent groups at the 2, 6 or 8 positions. Representative modified sugars include carbocyclic or acyclic sugars, sugars having substituent groups at their 2' position, and sugars having substituents in place of one or more hydrogen atoms of the sugar. Other altered base moieties and altered sugar moieties are disclosed in U.S. Pat. No. 3,687,808 and PCT application PCT/US89/02323.

Altered base moieties or altered sugar moieties also include other modifications consistent with the spirit of this invention. Such oligonucleotides are best described as moieties that are structurally distinguishable from yet functionally interchangeable with naturally occurring or synthetic wild type oligonucleotides. All such oligonucleotides are comprehended by this invention so long as they function effectively to mimic the structure of a desired RNA or DNA strand.

For use in antisense methodology, the oligonucleotides of the invention preferably comprise from about 10 to about 30 subunits. It is more preferred that such oligonucleotides comprise from about 15 to about 25 subunits. As will be appreciated, a subunit is a base and sugar combination suitably bound to adjacent subunits through a phosphorous-containing linkage. When used as "building blocks" in assembling oligonucleotides, even smaller assemblies are preferred.

It is preferred that the RNA or DNA portion which is to be modulated using oligonucleotides of the invention be preselected to comprise that portion of DNA or RNA which codes for the protein whose formation or activity is to be modulated. The targeting portion of the composition to be employed is, thus, selected to be complementary to the preselected portion of DNA or RNA, that is to be an antisense oligonucleotide for that portion.

In accordance with one preferred embodiment of this invention, the compounds of the invention hybridize to HIV mRNA encoding the tat protein, or to the TAR region of HIV mRNA. In another preferred embodiment, the compounds mimic the secondary structure of the TAR region of HIV mRNA, and by doing so bind the tat protein. Other preferred compounds are complementary to sequences for herpes, papilloma and other viruses.

The oligonucleotides of the invention can be used in diagnostics, therapeutics and as research reagents and kits. They can be used in pharmaceutical compositions by including a suitable pharmaceutically acceptable diluent or carrier. They further can be used for treating organisms having a disease characterized by the undesired production of a protein. The organism should be contacted with an oligonucleotide having a sequence that is capable of specifically hybridizing with a strand of nucleic acid coding for the undesirable protein. Treatments of this type can be practiced on a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the invention. Seemingly diverse organisms such as bacteria, yeast, protozoa, algae, all plants and all higher animal forms, including warm-blooded animals, can be treated. Further, since each cell of multicellular eukaryotes can be treated since they include both DNA-RNA transcription and RNA-protein translation as integral parts of their cellular activity. Furthermore, many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic oligonucleotides. As used herein, therapeutics is meant to include the eradication of a disease state, by killing an organism or by control of erratic or harmful cellular growth or expression.

In one aspect, the present invention is directed to synthetic methods wherein a protected nucleoside having formula I is contacted with a coupling reagent having formula $[(R_N)_2N]_2PO(CH_2)_xSi(R_S)_3$ for a time and under conditions effective to form a silylalkyl phosphoramidite monomer having formula II.

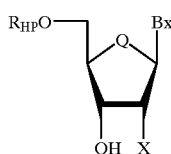

I

-continued

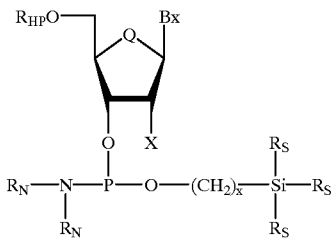

II

Such contacting preferably is effected under anhydrous conditions in the presence of a weak acid such as 1H-tetrazole, 5-(4-nitrophenyl)-1H-tetrazole, or diisopropylamino tetrazolide.

Q can be S, $CH_2$, CHF $CF_2$ or, preferably, O. See, e.g., Secrist, et al., Abstract 21, Synthesis and Biological Activity of 4'-Thionucleosides, Program & Abstracts, Tenth International Roundtable, Nucleosides, Nucleotides and their Biological Applications, Park City, Utah, Sep. 16–20, 1992. Each Q is independently selected and, hence, can be the same as or different from other Q within a given compound.

$B_X$ can be a nucleosidic base selected from adenine, guanine, uracil, thymine, cytosine, 2-aminoadenosine or 5-methylcytosine, although other non-naturally occurring species can be employed to provide stable duplex or triplex formation with, for example, DNA. Representative bases are disclosed in U.S. Pat. No. 3,687,808 (Merigan, et al.), which is incorporated herein by reference.

X can be H, OH, alkyl, substituted alkyl, alkaryl or aralkyl, F, Cl, Br, CN, $CF_3$, $OCF_3$, OCN, O-alkyl, S-alkyl, N-alkyl, O-alkenyl, S-alkenyl, N-alkenyl, $SOCH_3$, $SO_2CH_3$, $ONO_2$, $NO_2$, $N_3$, $NH_2$, heterocycloalkyl, heterocycloalkaryl, aminoalkylamino, polyalkylamino or substituted silyl, an RNA cleaving group, a group for improving the pharmacokinetic properties of an oligonucleotide, or a group for improving the pharmacodynamic properties of an oligonucleotide. It is intended that the term "alkyl" denote branched and straight chain hydrocarbonyl residues, including alkyl groups having one or more $^3H$ and/or $^{14}C$ atoms. It is preferred that X is H or OH, or, alternatively F, O-alkyl or O-alkenyl, especially where Q is O. Preferred alkyl and alkenyl groups have from 1 to about 10 carbon atoms.

$R_{HP}$ can be any hydroxyl protecting group. Preferably, $R_{HP}$ is stable under basic conditions but can be removed under acidic conditions. A wide variety of protecting groups can be employed in the methods of the invention. In general, protecting groups render chemical functionality inert to specific reaction conditions, and can be appended to and removed from such functionality in a molecule without substantially damaging the remainder of the molecule. Representative protecting groups are disclosed by Beaucage, et al., Tetrahedron 1992, 48, 2223. Preferred protecting groups include dimethoxytrityl (DMTr), monomethoxytrityl, 9-phenylxanthen-9-yl (Pixyl) and 9-(p-methoxyphenyl) xanthen-9-yl (Mox).

Coupling reagents having formulas $[(R_N)_2N]_2PO(CH_2)_xSi(R_S)_3$ preferably are prepared by reacting an alcohol having formula $HO(CH_2)_xSi(R_S)_3$ with phosphorus trichloride and reacting the resultant product, $Cl_2PO(CH_2)_xSi(R_S)_3$, with at least two equivalents of an amine having formula $(R_N)_2NH$. The $R_N$ groups can be the same or different and can be alkyl having 1 to about 10 carbon atoms, preferably 1 to 6 carbon atoms, more preferably 3 carbon atoms. Isopropyl groups are particularly preferred. The $R_S$ groups can be the same or different and can be alkyl having 1 to about 10 carbon atoms or aryl having 6 to about 10 carbon atoms. Preferably, $R_S$ is selected from methyl, ethyl, isopropyl, propenyl, n-butyl, t-butyl, and phenyl groups. Preferably, two $R_S$ are phenyl groups and one $R_S$ is a methyl group. The variable x can be 1 to about 7, preferably 1 to about 4, more preferably 2. A number of suitable alcohols are disclosed by U.S. Pat. No. 5,159,095, issued Oct. 27, 1992 in the name of Celebuski, which is incorporated herein by reference. One preferred coupling reagent is diphenylmethylsilylethyl N,N-diisopropylphosphoramidite, which can be derived from diphenylmethylsilylethyl alcohol via diphenylmethylsilylethyl phosphodichloridite.

Silylalkyl phosphoramidite monomers having formula II can be contacted with support-bound nucleosides having formula III for a time and under conditions effective to form phosphite dimers having formula IV, wherein (P) is H, a hydroxyl protecting group, or a solid support.

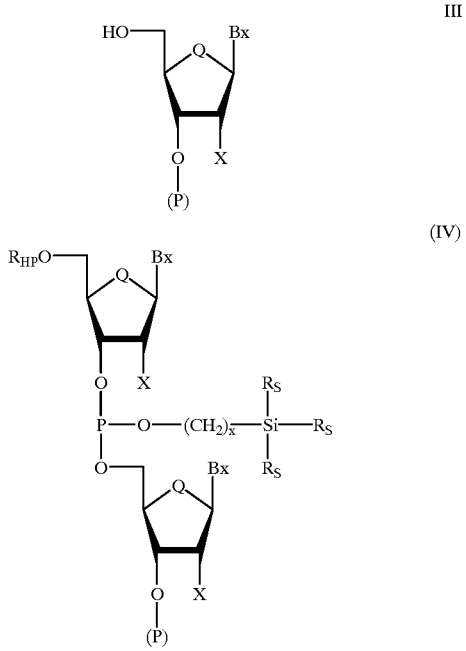

In preferred embodiments, such contact is effected under anhydrous conditions in the presence of an activating agent like 1H-tetrazole, 5-(4-nitrophenyl)-1H-tetrazole, or diisopropylamino tetrazolide.

Solid supports according to the invention include controlled pore glass (CPG), oxalyl-controlled pore glass (see, e.g., Alul, et al., *Nucleic Acids Research* 1991, 19, 1527), TentaGel Support—an aminopolyethyleneglycol derivatized support (see, e.g., Wright, et al., *Tetrahedron Letters* 1993, 34, 3373) or Poros—a copolymer of polystyrene/divinylbenzene.

Phosphite compounds having formula IV next are oxidized to produce, for example, compounds having formula V.

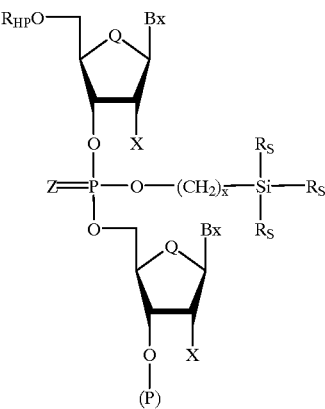

Such oxidation can be effected sequentially to form both phosphate (Z=O) and phosphorothioate (Z=S) precursor structures. Useful sulfurizing agents include Beaucage reagent (see e.g. Iyer, et al., *J. Am. Chem. Soc.* 1990, 112, 1253 and Iyer, et al., *J. Org. Chem.* 1990, 55, 4693), tetraethylthiuram disulfide (see e.g., Vu, et al., *Tetrahedron Letters* 1991, 32, 3005), dibenzoyl tetrasulfide (see e.g., Rao, et al., *Tetrahedron Letters* 1992, 33, 4839), di(phenylacetyl)disulfide (see e.g., Kamer, et al, *Tetrahedron Letters* 1989, 30, 6757), sulfur, sulfur in combination with ligands like triaryl or trialkyl or triaralkyl or trialkaryl phosphines. Useful oxidizing agents include iodine/tetrahydrofuran/water/pyridine or hydrogen peroxide/water or tert-butyl hydroperoxide or any peracid like m-chloroperbenzoic acid. In the case of sulfurization, reaction is performed under anhydrous conditions with the exclusion of air, in particular oxygen, whereas in the case of oxidation the reaction can be performed under aqueous conditions.

In certain embodiments, compounds having formula V are exposed to reaction conditions effective to remove the hydroxyl protecting group $R_{HP}$, and the resultant product then is coupled with additional monomer II to form phosphite oligonucleotides having formula Va (n=1). As will be recognized, further compounds having formula Va wherein n is, for example, 2–200, can be prepared by repeating the foregoing oxidation, deprotection, and coupling steps.

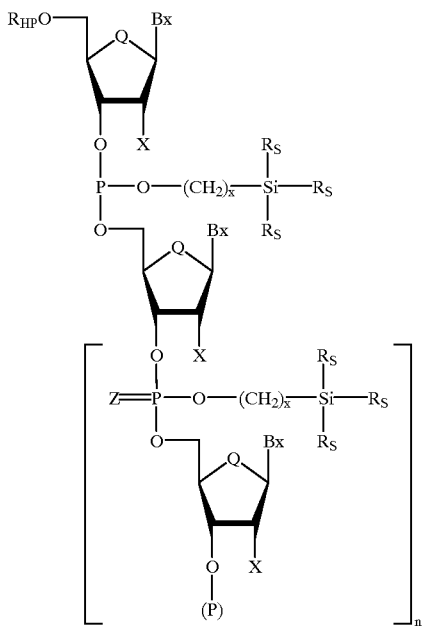

Va

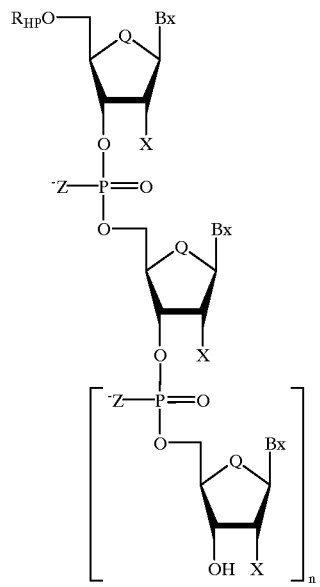

Via

Where (P) is a hydroxyl protecting group or a solid support, oxidation products having, for example, formula V can be exposed to conditions effective to cleave the protecting group or support. The resulting product is contacted with ammonium hydroxide or some other aqueous base or fluoride ion to remove the silylalkyl portion thereof to produce phosphate- and phosphorothioate-containing compounds having, for example, formula VI or VIa.

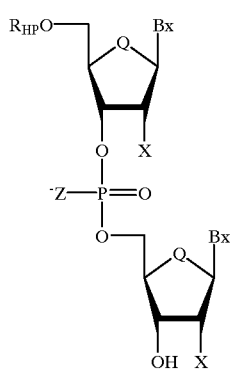

VI

Cleavage from solid supports such as controlled pore glass preferably is effected with ammonium hydroxide or some other aqueous base.

Contact with fluoride ion preferably is effected in a solvent such as tetrahydrofuran, acetonitrile, dimethoxyethane, or water. Fluoride ion preferably is provided in the form of one or more salts selected from tetraalkylammonium fluorides (e.g., tetrabutylammonium fluoride (TBAF)), potassium fluoride, or cesium fluoride.

The $R_{HP}$ group can be removed from compounds having formulas VI and VIa by techniques well known in the art to produce compounds having formulas VI and VIa wherein $R_{HP}$ is H. For example, dimethoxytrityl protecting groups can be removed by protic acids such as formic acid, dichloroacetic acid, trichloroacetic acid p-toluene sulfonic acid or any other acid or with Lewis acids like zinc bromide or any other Lewis acid.

As will be recognized, the process steps of the present invention need not be performed any particular number of times or in any particular sequence. Also, cleavage of compounds of the invention from solid supports can precede or follow removal of silylalkyl groups.

Additional objects, advantages, and novel features of this invention will become apparent to those skilled in the art upon examination of the following examples thereof, which are not intended to be limiting.

EXAMPLE 1

Preparation of Diphenylmethylsilylethyl N,N-Diisopropylphosphoramidite

A 500 mL three-necked flask equipped with a magnetic stirrer, a glass stopper, and an inlet for argon is assembled under argon atmosphere. All glassware are dried in an oven at 120° C. for 1 hour. The reaction flask is charged with anhydrous ether (150 mL) and phosphorous trichloride (9.27 g; 67.5 mmol). Diphenylmethylsilyl ethanol (12.12 g; 50 mmol) in ether (50 mL) is added to the reaction flask slowly with stirring at 0° C. (ice cooling) using pressure-equalized addition funnel. After addition is complete, the ice bath is removed and the reaction is stirred for three hours. The reaction mixture then is transferred to a 500 mL flask and concentrated under reduced pressure.

To this colorless product in anhydrous ether (200 mL) is added diisopropylamine (57.7 mL) at 0° C. under argon. After the addition is complete, stirring is continued at room temperature for 16 hours (overnight). The reaction mixture is filtered and concentrated to afford a colorless viscous liquid. $^{31}$P NMR (CDCl$_3$) of this product shows a major peak at δ 123.4 ppm.

EXAMPLE 2

Preparation of Protected Silylalkyl Phosphoramidite Monomers

A. 5'-O-(4,4'-dimethoxytrityl)thymidine-3-O-(2-diphenylmethylsilylethyl N,N-diisopropylphosphoramidite).

A 250 mL two-necked flask equipped with a magnetic stirrer, a gas inlet for argon, and a septum is assembled under an argon atmosphere. All glassware are dried at 120° C. for 1 hour. The flask is charged with 5'-O-( 4,4'-dimethoxytrityl) thymidine (Chem-Impex; 3.81 g; 7 mmol) and 5-(4-nitrophenyl)-1H-tetrazole (Chem-Impex; 1.07 g; 5.6 mmol). Anhydrous acetonitrile (50 mL) is added. To this stirred mixture under argon at room temperature is added a solution of diphenylmethylsilylethyl N,N-diisopropylphosphoramidite (4.96 g; 10.5 mmol) in acetonitrile (50 mL). After stirring for two hours, thin layer chromatography on Whatman Silica Gel 60A Diamond KGF (100% ethyl acetate) shows disappearance of starting nucleoside. The reaction mixture is filtered and the filtrate diluted with ethyl acetate (100 mL), washed once with cold saturated sodium bicarbonate solution, brine and dried (MgSO$_4$). The dried solution is concentrated under reduced pressure to afford a viscous foamy liquid. The crude product is purified by flash chromatography using silica gel. A gradient solvent system consisting of ethyl acetate and hexane is used. Triethylamine (1%) is used throughout the purification. The fractions corresponding to the product are combined and concentrated to afford a pale yellow viscous foamy liquid (9.87 g; 77%). $^{31}$P NMR (CDCl$_3$) shows two signals at δ 145.483, 146.176 corresponding to two diastereomeric products.

B. N$^2$-Isobutyryl-5'-O-(4,4'-dimethoxytrityl)-2'-deoxyguanosine-3'-O-(2-diphenylmethylsilylethyl N,N-diisopropyl-phosphoramidite).

A 250 mL two-necked flask equipped with a magnetic stirrer, a gas inlet for argon, and a septum is assembled under an argon atmosphere. All glassware are dried at 120° C. for 1 hour. The flask is charged with N$^2$-Isobutyryl-5'-O-(4,4'-di-methoxytrityl)-2'-deoxyguanosine (Chem-Impex; 3.195 g; 5 mmol) and diisopropyl ammonium tetrazolide (0.684 g; 4 mmol). Anhydrous acetonitrile (50 mL) is added. To this stirred mixture under argon at room temperature is added a solution of diphenylmethylsilylethyl N,N-diisopropylphosphoramidite (3.543 g; 7.5 mmol) in acetonitrile (50 mL). After stirring for two hours, thin layer chromatography on Whatman Silica Gel 60A Diamond KGF (100% ethyl acetate) shows disappearance of starting nucleoside. The reaction mixture is filtered and the filtrate diluted with ethyl acetate (100 mL), washed once with cold saturated sodium bicarbonate solution, brine and dried (MgSO$_4$). The dried solution is concentrated under reduced pressure to afford a viscous foamy liquid. The crude product is purified by flash chromatography using silica gel. A gradient solvent system consisting of ethyl acetate and hexane is used. Triethylamine (1%) is used throughout the purification. The fractions corresponding to the product are combined and concentrated to afford a pale yellow viscous foamy liquid (3.6 g; 65%). $^{31}$P NMR (CDCl$_3$) shows two signals at δ 145.483, 146.176 corresponding to two diastereomeric products.

C. N$^6$-Benzoyl-5'-O-(4,4'-dimethoxytrityl)-2'-deoxyadenosine-3'-O-(2-diphenylmethylsilylethyl N,N-diisopropylphos-phoramidite).

A 250 mL two-necked flask equipped with a magnetic stirrer, a gas inlet for argon, and a septum is assembled under an argon atmosphere. All glassware are dried at 120° C. for 1 hour. The flask is charged with N$^6$-benzoyl-5'-O-(4,4'-dimethoxytrityl)-2'-deoxyadenosine (Chem-Impex; 3.285 g; 5 mmol) and diisopropylammonium tetrazolide (0.684 g; 4 mmol). Anhydrous acetonitrile (50 mL) is added. To this stirred mixture under argon at room temperature is added a solution of diphenylmethylsilylethyl N,N-diisopropylphosphoramidite (2.835 g; 6 mmol) in acetonitrile (50 mL). After stirring for two hours, the reaction mixture is filtered and concentrated to afford a viscous foamy material. The crude product is purified by flash chromatography using silica gel. A gradient solvent system consisting of ethyl acetate and hexane is used. Triethylamine (1%) is used throughout the purification. The fractions corresponding to the product are combined and concentrated to afford a viscous foamy liquid (3.81 g; 68%). $^{31}$P NMR (CDCl$_3$) shows two signals at δ 146.093, 146.478 corresponding to two diastereomeric products.

D. N$^4$-Benzoyl-5'-O-(4,4'-dimethoxytrityl)-2'-deoxycytidine-3'-O-(2-diphenylmethylsilylethyl N,N-diisopropylphos-phoramidite).

A 250 mL two-necked flask equipped with a magnetic stirrer, a gas inlet for argon, and a septum is assembled under an argon atmosphere. All glassware are dried at 120° C. for 1 hour. The flask is charged with N$^4$-benzoyl-5'-O-(4,4'-dimethoxytrityl)-2'-deoxycytidine (Chem-Impex; 3.169 g; 5 mmol) and diisopropylammonium tetrazolide (0.684 g; 4 mmol). Anhydrous acetonitrile (50 mL) is added. To this stirred mixture under argon at room temperature is added a solution of diphenylmethylsilylethyl N,N-diisopropylphosphoramidite (3.543 g; 7.5 mmol) in acetonitrile (50 mL). After stirring for two hours, thin layer chromatography on Whatman Silica Gel 60A Diamond KGF (100% ethyl acetate) shows disappearance of starting nucleoside. The reaction mixture is filtered and the filtrate diluted with ethyl acetate (100 mL), washed once with cold saturated sodium bicarbonate solution, brine and dried (MgSO$_4$). The dried solution is concentrated under reduced pressure to afford a viscous foamy liquid. The crude product is purified by flash chromatography using silica gel. A gradient solvent system consisting of ethyl acetate and hexane is used. Triethylamine (1%) is used throughout the purification. The fractions corresponding to the product are combined and concentrated to afford a viscous foamy liquid (4.09 g; 74%). $^{31}$P NMR (CDCl$_3$) shows two signals at δ 146.277, 146.682 corresponding to two diastereomeric products.

EXAMPLE 3

Coupling Procedures

A. Synthesis of T-T Phosphorothioate Dimer.

5'-O-Dimethoxytritylthymidine (100 mg, 4 mmole) bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with dichloromethane and then with acetonitrile. Then, a 0.2 M solution of 5'-O-(4,4'-dimethoxytrityl)thymidine-3'-O-(2-diphenylmethylsilylethyl N,N-diisopropylphosphoramidite) in acetonitrile and a 0.4 M solution of 1H-tetrazole in acetonitrile are added and reacted at room temperature for 5 minutes. The product is washed with acetonitrile. Then, a 0.05 M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the unreacted 5'-hydroxyl group. The product is washed with acetonitrile.

The carrier containing the compound is treated with 30% aqueous ammonium hydroxide solution for 90 minutes. The aqueous solution is filtered, concentrated under reduced pressure, and then treated at room temperature with 1.0 M solution of tetra-n-butyl ammonium fluoride in THF to give a phosphorothioate dimer of T-T.

B. Synthesis of C-T Phosphorothioate Dimer.

5'-O-Dimethoxytritylthymidine (100 mg, 4 mmole) bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with acetonitrile. Then, a 0.2 M solution of $N^4$-Benzoyl-5'-O-(4,4'-dimethoxytrityl)-2'-deoxycytidine-3'-O-(2-diphenylmethylsilylethyl N,N-diisopropylphosphoramidite) in acetonitrile and a 0.4 M solution of 1H-tetrazole in acetonitrile are added and reacted at room temperature for 5 minutes. The product is washed with acetonitrile, and then a 0.05 M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the unreacted 5'-hydroxyl group. The product is washed with acetonitrile.

The carrier containing the compound is treated with 30% aqueous ammonium hydroxide solution for 90 minutes and then incubated at 55° C. for 12 hours. The aqueous solution is filtered, concentrated under reduced pressure to give a phosphorothioate dimer of dC-T.

C. Synthesis of T-T Phosphodiester Dimer.

5'-O-Dimethoxytritylthymidine (100 mg, 4 mmole) bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with dichloromethane and then with acetonitrile. Then, a 0.2 M solution of 5'-O-(4,4'-dimethoxytrityl)thymidine-3'-O-(2-diphenyl-methylsilylethyl N,N-diisopropylphosphoramidite) in acetonitrile and a 0.4 M solution of 1H-tetrazole in acetonitrile are added and reacted at room temperature for 5 minutes. The product is washed with acetonitrile, and then a 0.1 M iodine in water/pyridine/THF (2/20/80) is added and reacted at room temperature for 5 minutes. The support is washed with acetonitrile and then a solution of acetic anhydride/lutidine/THF (1:1:8), and N-methyl imidazole/THF is added to cap the unreacted 5'-hydroxyl group. The product is washed with acetonitrile.

The carrier containing the compound is treated with 30% aqueous ammonium hydroxide solution for 90 minutes at room temperature and then incubated at 55° C. for 1 hour. The aqueous solution is filtered, concentrated under reduced pressure to give a T-T phosphodiester dimer.

D. Synthesis of 5'-TTTTTTT-3' Phosphorothioate Heptamer.

5'-O-Dimethoxytritylthymidine (50 mg, 2 mmole) bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with acetonitrile. Then, a 0.2 M solution of 5'-O-(4,4'-dimethoxytrityl)thymidine-3'-O-(2-diphenylmethylsilylethyl N,N-diisopropylphosphoramidite) in acetonitrile and a 0.4 M solution of 1H-tetrazole in acetonitrile are added and reacted at room temperature for 5 minutes. The product is washed with acetonitrile, and then a 0.05 M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the unreacted 5'-hydroxyl group. The product is washed with acetonitrile.

This complete cycle is repeated five more times to get the completely protected thymidine heptamer. The carrier containing the compound is treated with 30% aqueous ammonium hydroxide solution for 90 minutes at room temperature and then incubated at 55° C. for 1 hour. The aqueous solution is filtered, concentrated under reduced pressure to give a phosphorothioate heptamer of TTTTTTT.

E. Synthesis of 5'-d(GACT)-3' Phosphorothioate Tetramer.

5'-O-Dimethoxytritylthymidine (50 mg, 2 mmole) bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with acetonitrile. Then, a 0.2 M solution of 5'-O-(4,4'-dimethoxytrityl)thymidine-3'-O-(2-diphenylmethylsilylethyl N,N-diisopropylphosphoramidite) in acetonitrile and a 0.4 M solution of 1H-tetrazole in acetonitrile is added, and reacted at room temperature for 5 minutes. The product is washed with acetonitrile, and then a 0.05 M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the unreacted 5'-hydroxyl group. The product is washed with acetonitrile.

A dichloromethane solution of 2% dichloroacetic acid (volume/volume) is added to deprotect the 5'-hydroxyl group. The product is washed with acetonitrile. Then, a 0.2 M solution of $N^4$-benzoyl-5'-O-(4,4'-dimethoxytrityl)-2'-deoxycytidine-3'-O-(2-diphenylmethylsilylethyl N,N-diisopropylphosphoramidite) in acetonitrile and a 0.4 M solution of 1H-tetrazole in acetonitrile is added, and reacted at room temperature for 5 minutes. The product is washed with acetonitrile, and then a 0.05 M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/

THF (1:1:8), and N-methyl imidazole/THF is added to cap the unreacted 5'-hydroxyl group. The product is washed with acetonitrile.

A dichloromethane solution of 2% dichloroacetic acid (volume/volume) is added to deprotect the 5'-hydroxyl group. The product is washed with acetonitrile. Then, a 0.2 M solution of $N^6$-benzoyl-5'-O-(4,4'-dimethoxytrityl)-2'-deoxyadenosine-3'-O-(2-diphenylmethylsilylethyl N,N-diisopropylphosphoramidite) in anhydrous acetonitrile and a 0.4M solution of 1H-tetrazole in acetonitrile is added, and reacted at room temperature for 5 minutes. The product is washed with acetonitrile, and then a 0.05 M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the unreacted 5'-hydroxyl group. The product is washed with acetonitrile.

A dichloromethane-solution of 2% dichloroacetic acid (volume/volume) is added to deprotect the 5'-hydroxyl group. The product is washed with acetonitrile. Then, a 0.2 M solution of $N^2$-isobutyryl-5'-O-(4,4'-dimethoxytrityl)-2'-deoxyguanosine-3'-O-(2-diphenylmethylsilylethyl N,N-diisopropylphosphoramidite) in acetonitrile and a 0.4 M solution of 1H-tetrazole in acetonitrile is added, and reacted at room temperature for 5 minutes. The product is washed with acetonitrile, and then a 0.05 M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the unreacted 5'-hydroxyl group. The product is washed with acetonitrile.

The carrier containing the compound is treated with 30% aqueous ammonium hydroxide solution for 90 minutes at room temperature and then incubated at 55° C. for 24 hour. The aqueous solution is filtered, concentrated under reduced pressure to give a phosphorothioate tetramer of 5'-dG-dA-dC-T-3'.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A synthetic process comprising contacting a compound having formula I with a coupling reagent having formula $[(R_N)_2N]_2PO(CH_2)_xSi(R_S)_3$ for a time and under reaction conditions effective to form a compound having formula II:

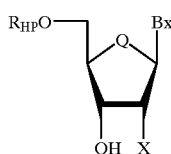

I

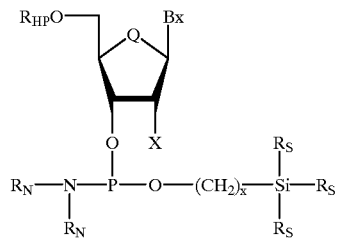

II wherein:
each Q is, independently, O, S, $CH_2$, CHF or $CF_2$;
each $B_x$ is, independently, a nucleosidic base;
each X is, independently, H, OH, alkyl, substituted alkyl, alkaryl or aralkyl, F, Cl, Br, CN, $CF_3$, $OCF_3$, OCN, O-alkyl, S-alkyl, N-alkyl, O-alkenyl, S-alkenyl, N-alkenyl, $SOCH_3$, $SO_2CH_3$, $ONO_2$, $NO_2$, $N_3$, $NH_2$, heterocycloalkyl, heterocycloalkaryl, aminoalkylamino, polyalkylamino or substituted silyl;
$R_{HP}$ is a hydroxyl protecting group;
each $R_N$ is, independently, alkyl having 1 to about 10 carbon atoms;
each $R_S$ is, independently, alkyl having 1 to about 10 carbon atoms or aryl having 6 to about 10 carbon atoms; and
x is 1 to about 7.

2. The process of claim 1 further comprising contacting said compound having formula II with a compound having formula III for a time and under reaction conditions effective to form a compound having formula IV:

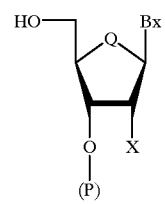

III

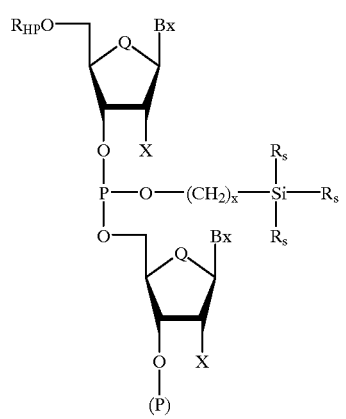

IV wherein (P) is H, a hydroxyl protecting group or a solid support.

3. The process of claim 2 further comprising contacting said compound having formula IV with an oxidizing agent for a time and under reaction conditions effective to form a compound having formula V:

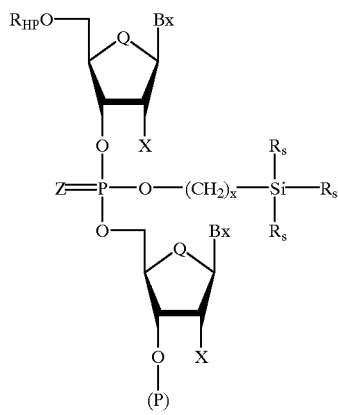

wherein Z is O or S.

4. The process of claim 3 further comprising contacting said compound having formula V and where (P) is a solid support with aqueous base to form a solution-phase reaction product.

5. The process of claim 4 further comprising contacting said solution-phase reaction product with fluoride ion to produce a compound having formula VI:

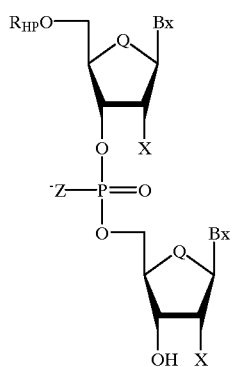

6. The process of claim 5 further comprising exposing said compound having formula VI to conditions effective to remove said $R_{HP}$ group.

7. The process of claim 3 further comprising contacting said compound having formula V with fluoride ion to remove the silylalkyl phosphate protecting group.

8. The process of claim 7 further comprising contacting said compound having said silylalkyl phosphate protecting group removed therefrom with aqueous base to form a compound having formula VI:

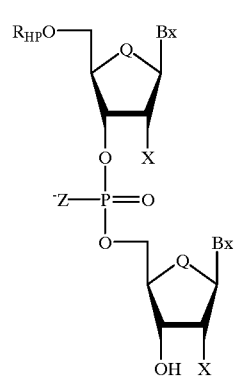

9. The process of claim 8 further comprising exposing said compound having formula VI to conditions effective to remove said $R_{HP}$ group.

* * * * *